United States Patent [19]

Hatzenbuhler et al.

[11] Patent Number: 4,558,093
[45] Date of Patent: Dec. 10, 1985

[54] LASER BARRIER

[76] Inventors: John R. Hatzenbuhler, 1917 E. Kenmore Pl., Shorewood, Wis. 53211; Thomas A. Lindl, 3325 W. Juneau Ave., Milwaukee, Wis. 53208

[21] Appl. No.: 605,206

[22] Filed: Apr. 30, 1984

[51] Int. Cl.[4] ............. C08J 9/32; C08K 3/20; C08K 7/28; C08L 83/04
[52] U.S. Cl. ............. 524/837; 128/DIG. 21; 521/63; 521/154; 523/219; 604/21; 604/23; 604/369; 604/372; 524/838
[58] Field of Search ............. 523/219; 524/837, 838; 521/63, 154; 106/287.13

[56] References Cited

U.S. PATENT DOCUMENTS

| | | |
|---|---|---|
| 3,039,001 | 6/1962 | Park et al. . |
| 3,296,161 | 1/1967 | Kulpa . |
| 3,382,205 | 5/1968 | Beers . |
| 3,720,836 | 3/1973 | Donges et al. . |
| 3,871,739 | 3/1975 | Poulsen . |
| 3,919,136 | 11/1975 | Smith ............. 524/837 |
| 3,933,712 | 1/1976 | Vanaglash ............. 523/219 |
| 3,960,754 | 6/1976 | Woodcock . |
| 4,000,108 | 12/1976 | Yokdkawa ............. 523/219 |
| 4,072,635 | 2/1978 | Jeram ............. 523/219 |
| 4,079,162 | 3/1978 | Metzger ............. 523/219 |
| 4,114,985 | 9/1978 | Friedman . |
| 4,203,886 | 5/1980 | Hirai et al. . |
| 4,389,452 | 6/1983 | Chahroudi et al. . |
| 4,396,643 | 8/1983 | Kuehn et al. . |
| 4,433,069 | 2/1984 | Harper ............. 523/219 |

OTHER PUBLICATIONS

Chemical Abstracts, vol. 69, 9168, No. 19873h, p. 1882.
Chemical Abstracts, vol. 74, 1971, No. 19913c, p. 34.
Chemical Abstracts, vol. 88, 1978, No. 196755j, p. 348.
Chemical Abstracts, vol. 93, 1980, No. 93: 16774m.

Primary Examiner—C. Warren Ivy
Attorney, Agent, or Firm—Andrus, Sceales, Starke & Sawall

[57] ABSTRACT

A laser shield consists essentially of a series of spherical glass bubbles densely packed within a range of $1.95 \times 10^3$ bubbles per cubic centimeter to $1.25 \times 10^8$ bubbles per cubic centimeter encapsulated in a matrix of silicone to provide a flexible and lightweight foam-like material to terminate $CO_2$ laser radiation without producing a substantial carbon plume. The glass bubbles may be filled with a gas. In another embodiment, a laser shield consists essentially of water encapsulated in a matrix of silicone to provide a flexible and lightweight material to terminate $CO_2$ laser radiation without producing a substantial carbon plume. In another embodiment, water bubbles and glass bubbles are both encapsulated within a matrix of silicone to provide a laser shield. A surgical drape, a surgical sponge and an endotracheal tube are formed of a flexible and lightweight material of a series of densely packed bubbles encapsulated in a matrix of silicone to terminate laser radiation.

4 Claims, 17 Drawing Figures

LASER BARRIER

TECHNICAL FIELD

This invention relates to a laser shield.

BACKGROUND

High powered infrared lasers have been widely used for a number of different applications. For example, lasers are now being widely used for medical therapy and surgical techniques wherein tissues are repaired and/or removed through the use of high energy lasers, such as produced by $CO_2$ (10.6 um wave length) lasers operating at irradiance levels of about one kw/cm$^2$ and higher.

A need exists to provide protection in areas where high energy lasers are being used to prevent burning of tissue or objects. Solid metallic shields used to absorb or reflect laser radiation are frequently not adaptable to many situations.

It is therefore desirable not only to protect personnel and other surrounding objects from incoming laser radiation, but it is also desirable to be able to terminate such laser radiation with a substance which may be readily formed into many shapes and is flexible so as to be manipulated for a wide variety of applications and uses.

BRIEF SUMMARY OF THE INVENTION

A laser shield is formed of densely packed bubbles which are encapsulated within a matrix of silicone for providing protection from laser radiation.

In one form, the bubbles consist of glass bubbles which reflect and refract laser energy to such a degree that the silicone diffuses the laser energy without producing a substantial carbon plume. Such glass bubbles may, if desired, be filled with a gas, such as argon or helium for example, which further produces an absorbing effect upon the incoming laser radiation.

In another form, the laser shield consists essentially of water encapsulated in a matrix of silicone to provide a flexible material to terminate $CO_2$ laser radiation without producing a substantial carbon plume. The water can be formed in layers surrounded by the silicone or it can be stirred into the silicone to produce numerous bubbles which are densely packed and encapsulated by the silicone matrix.

In still another form, water bubbles and glass bubbles are both combined and encapsulated by the silicone to provide a laser terminating shield.

The bubbles are densely packed within a range of $1.95 \times 10^3$ bubbles per cubic centimeter to $1.25 \times 10^8$ bubbles per cubic centimeter.

A surgical drape includes a flexible and lightweight sheet-like material to be applied adjacent to an area subject to laser radiation and is formed of a series of densely packed bubbles encapsulated in a matrix of silicone to terminate laser radiation. A fabric sheet is attached to the laser terminating material for comfort an aesthetic appearance.

A surgical sponge includes a flexible and lightweight sheet-like material formed of a series of densely packed bubbles encapsulated in a matrix of silicone to terminate laser radiation and is attached to a sponge-like surface to be applied adjacent to an area subject to laser radiation. Sheet-like sponges are connected to opposite sides of the sheet-like laser terminating material so as to sandwich the laser terminating material between the two sheet-like sponges.

An endotracheal tube for insertion into the esophagus of a mammal includes an elongated tube having first and second oppositely spaced openings to permit the passage of anesthetic gases which may be combustible or support combustion therethrough and is formed of a flexible and lightweight material having a series of densely packed bubbles encapsulated in a matrix of silicone to terminate laser radiation that may strike such elongated tube.

Other aspects of the invention will be made apparent in the drawings and photographs annexed hereto and the following description thereof as well as in the claims annexed hereto.

BEST MODE FOR CARRYING OUT THE INVENTION

A laser shield 20 includes a matrix of silicone 21 which encapsulates a series of densely packed bubbles 22 for terminating laser radiation.

The silicone 21 may be selected from any one of a number of commercially available silicones, such as curable organopolysiloxanes commercially sold as RTV silicone rubber sealers designed to be used as adhesive sealants under the designations RTV/112 and RTV/118 by the General Electric Co. of Waterford, N.Y., which claims such silicone to be within the scope of U.S. Pat. Nos. 3,296,161 and 3,382,205.

In one form, the silicone is conformed to enclose water and is thereafter cured to encapsulate the water within the silicone to provide a flexible material which effectively terminates $CO_2$ laser radiation.

Figure 1:
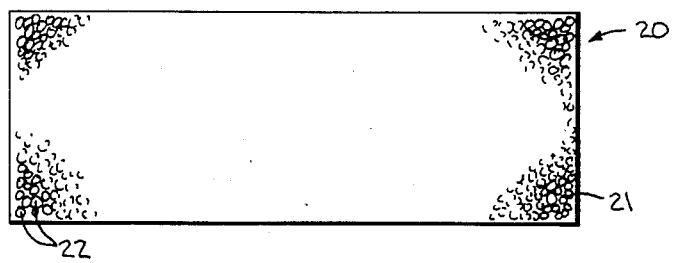
FIG. 1 is a diagramatic cross-sectioned illustration showing a series of densely packed bubbles encapsulated in a matrix of silicone.
Figure 11:
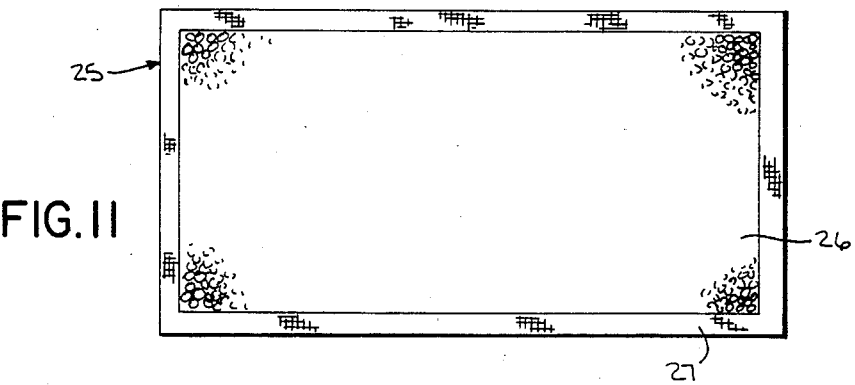
FIG. 11 is a top view diagramatic illustration of a surgical drape which includes a laser terminating material.
Figure 12:
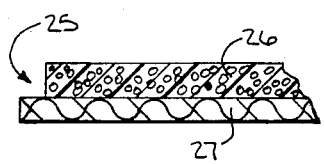
FIG. 12 is a side elevational view of the surgical drape of FIG. 11.
Figure 13:
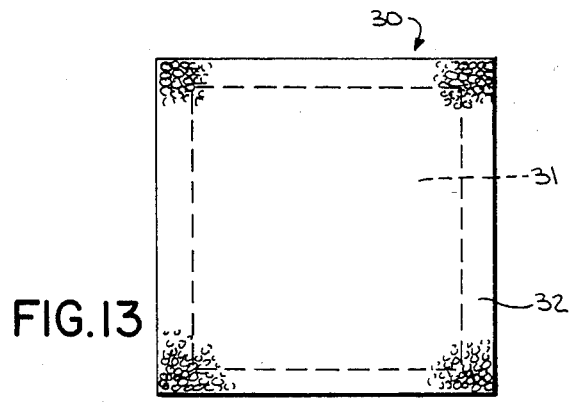
FIG. 13 is a top diagramatic illustration of a surgical sponge containing a laser terminating material.
Figure 14:
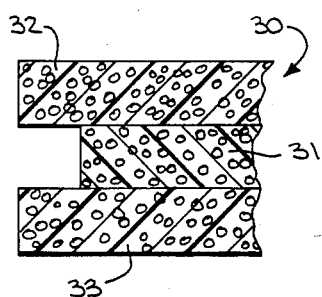
FIG. 14 is a side elevational view of the surgical sponge of FIG. 13.
Figure 2:
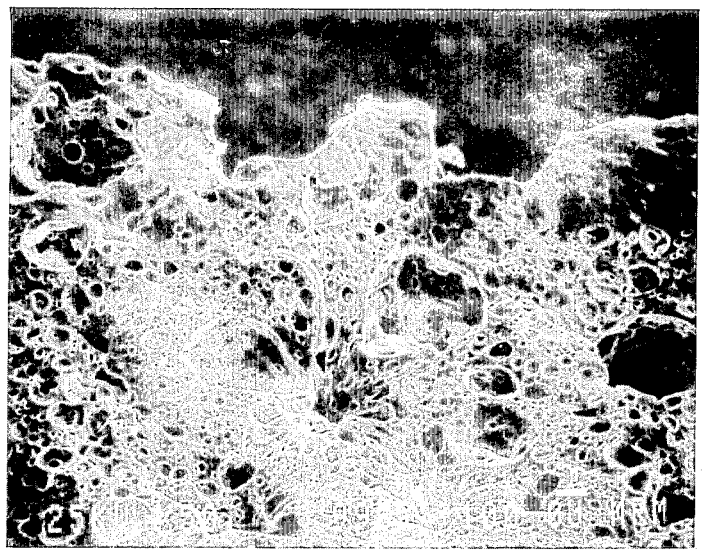
FIG. 2 is a black and white photo-micrograph showing the microstructure of a laser shield consisting of water encapsulated in a matrix of silicone.
Figure 3:
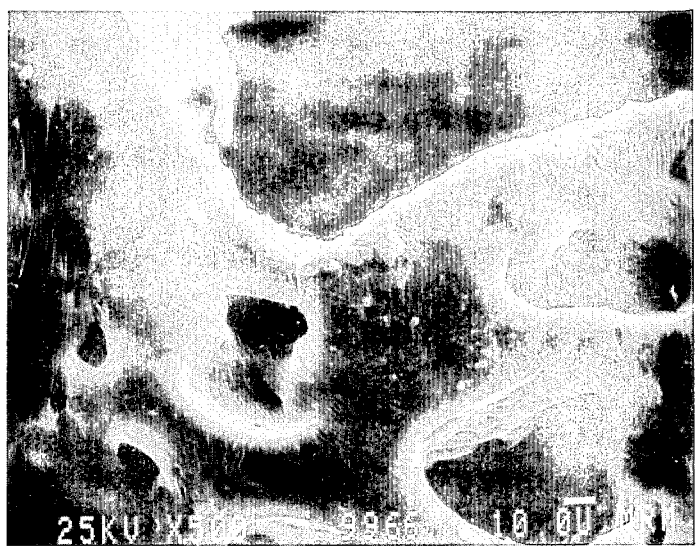
FIG. 3 is a black and white photo-micrograph showing a greater magnification of a portion of the laser shield shown in FIG. 2.
Figure 4:
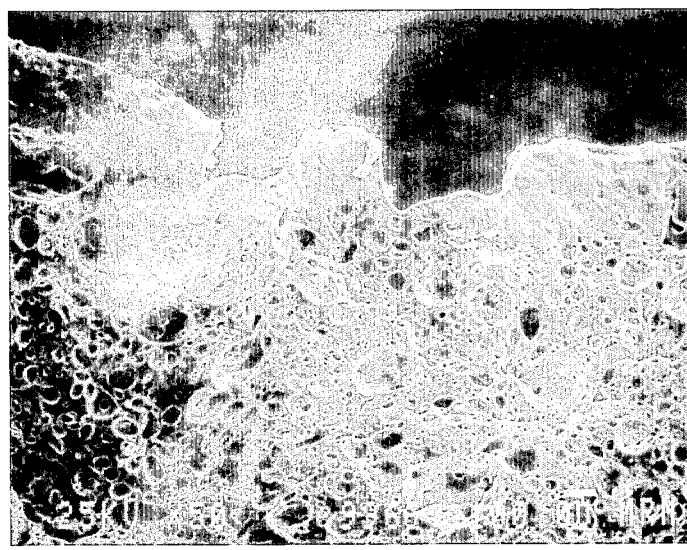
FIG. 4 is a black and white photo-micrograph duplicate of FIG. 2 and shows the microstructure of the laser shield after terminating laser energy.

One embodiment encapsulates water in a layer between two layers of silicone to provide a sandwiched effect of the water between and surrounded by silicone. Another embodiment requires mixing or stirring the water into the silicone to produce water bubbles or droplets throughout the silicone to provide a series of densely packed water bubbles which are encapsulated in a matrix of silicone. This later embodiment is photographically shown in FIG. 2 wherein a cut-away portion of the laser shield shows openings where water bubbles or droplets had been entrapped by the surrounding silicone. The picture of FIG. 3 shows a close-up of a portion of the laser shield. The picture of FIG. 4 shows where laser energy evaporated and molded a portion of the laser shield which effectively terminated such laser energy within the confines of the laser shield.

It is also contemplated that a solvent, such as mineral spirits may be added with the water and encapulated by the silicone to function as an inert element when cured without effecting the laser terminating properties of the shield.

By way of example and for illustrative purposes only, a laser shield may be formulated with one part of water and one part of mineral spirits encapsulated by one part of silicone.

In an alternative embodiment, the bubbles 22 are provided by a series of densely packed spherical glass bubbles which are encapsulated in the matrix silicone to provide a flexible and lightweight foam-like material which terminates $CO_2$ laser radiation without producing a substantial carbon plume. Such glass bubbles may be selected from any one of a number of commercially available glass bubbles such as marketed by 3M of St. Paul, Minn. as its "general purpose series". The glass bubbles are selected from a range of 20 microns to 200 microns and are densely packed when encapsulated within the silicone. The bubbles should be densely packed within a range of from $1.95 \times 10^3$ bubbles per each cubic centimeter to $1.25 \times 10^8$ bubbles per each cubic centimeter. The glass bubbles are generally selected from a size range of from 20 microns to 200 microns.

Figure 5:
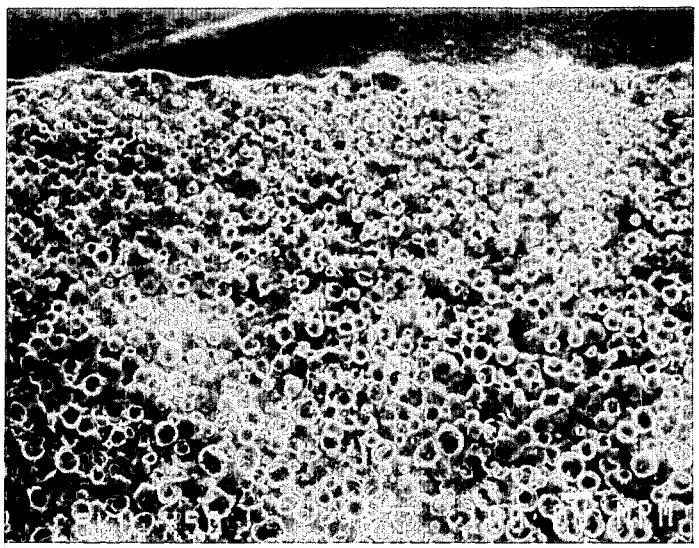
FIG. 5 is a balck and white photo-micrograph showing the microstructure of a laser shield consisting of glass bubbles encapsulated in a matrix of silicone.
Figure 6:
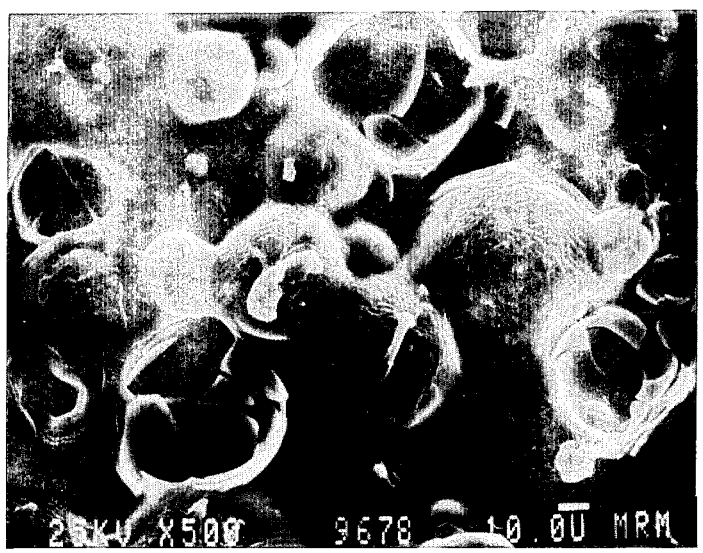
FIG. 6 is a black and white photo-micrograph showing a greater magnification of a portion of the laser shield shown in FIG. 5.
Figure 7:
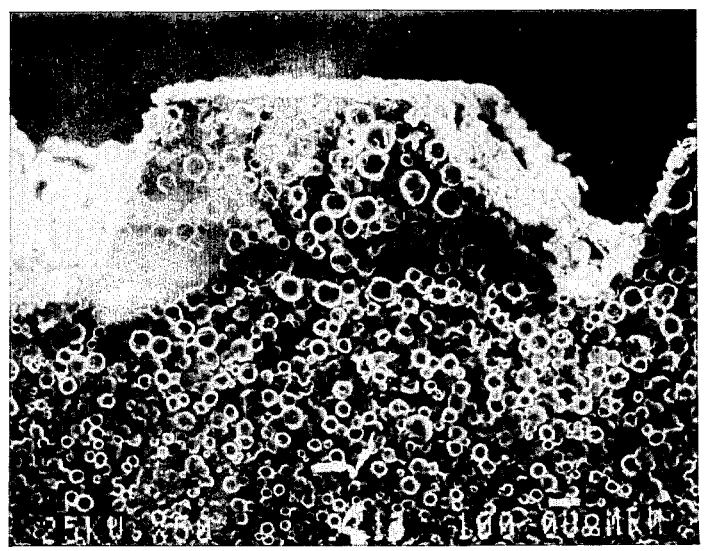
FIG. 7 is a black and white photo-micrograph showing the microstructure of the laser shield of FIG. 5 after terminating laser energy.

The picture of FIG. 5 illustrates densely packed glass bubbles which are encapsulated in a matrix of silicone. The picture of FIG. 6 is of higher magnification and it is noted that the broken glass bubbles were caused when cutting the laser shield in order to take the magnified picture. The micro-photograph of FIG. 7 shows another view of the laser shield of FIG. 5 which has terminated two bursts of laser energy. Laser energy at 80 watts has been found to be terminated within 0.6 to 0.9 millimeters of penetration into the laser shield.

By way of example and for illustrative purposes only, a laser shield may be formulated with 30 milliliters of silicone which encapsulates 18 milliliters of glass bubbles. Alternatively, 30 milliliters of silicone may be used in combination with 18 milliliters of glass bubbles and 30 milliliters of a solvent such as mineral spirits to encapsulate the glass bubbles within the silicone.

Figure 8:
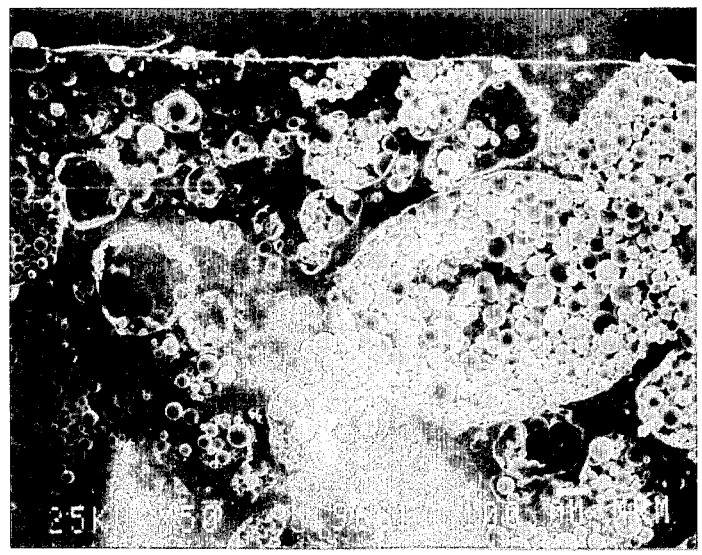
FIG. 8 is a black and white photo-micrograph showing the microstructure of a laser shield consisting of water and glass bubbles encapsulated in a matrix of silicone.
Figure 9:
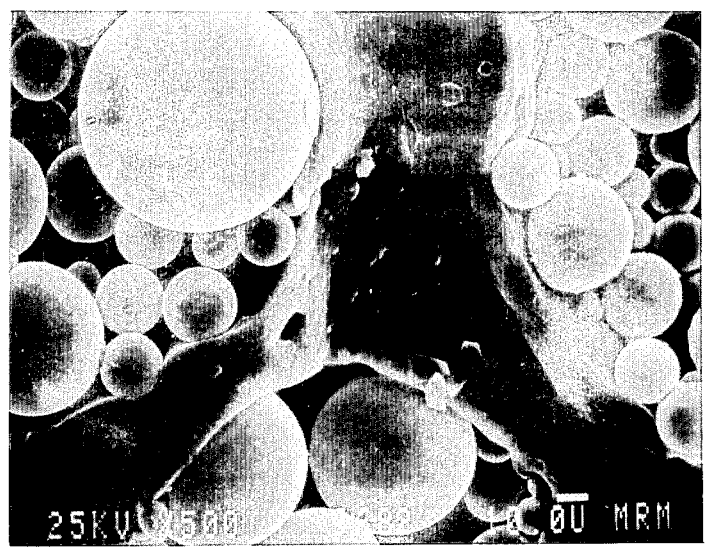
FIG. 9 is a black and white photo-micrograph showing a greater magnification of a portion of the laser shield shown in FIG. 8.
Figure 10:
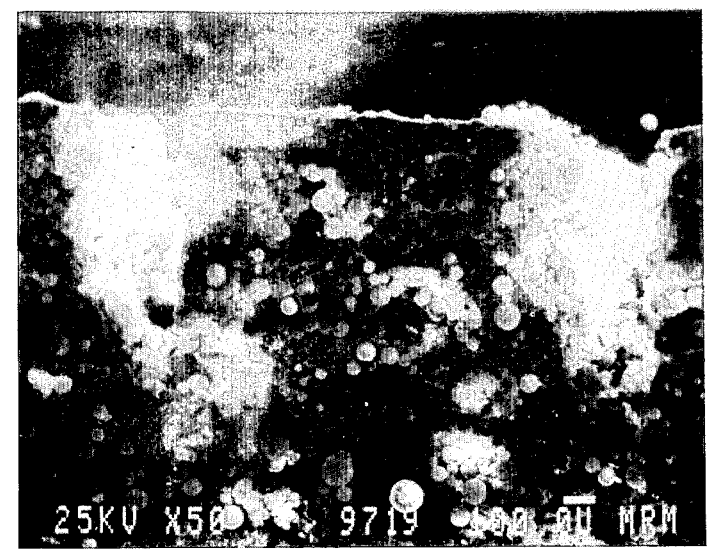
FIG. 10 is a black and white photo-micrograph showing the micro structure of the laser shield of FIG. 8 after terminating laser energy.
Figure 15:
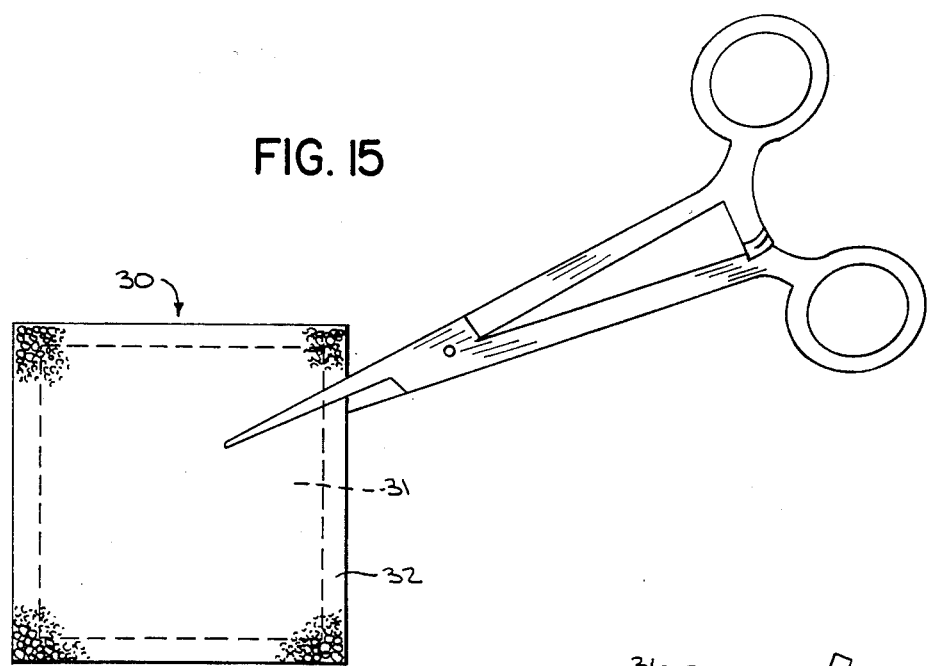
FIG. 15 is another top diagramatic illustration of the surgical sponge of FIG. 13 and illustrating the application of forceps thereto.
Figure 16:
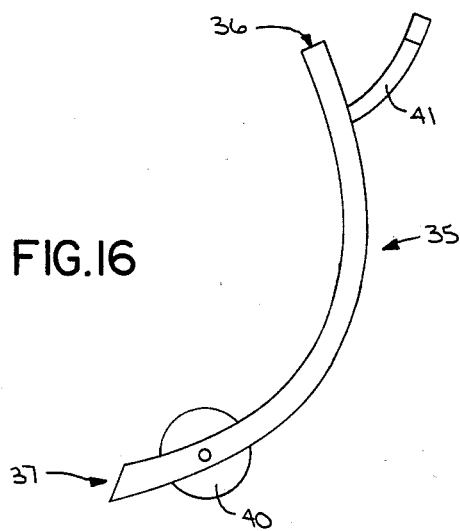
FIG. 16 is a diagramatic illustration of an endotracheal tube formed of a laser terminating material.
Figure 17:
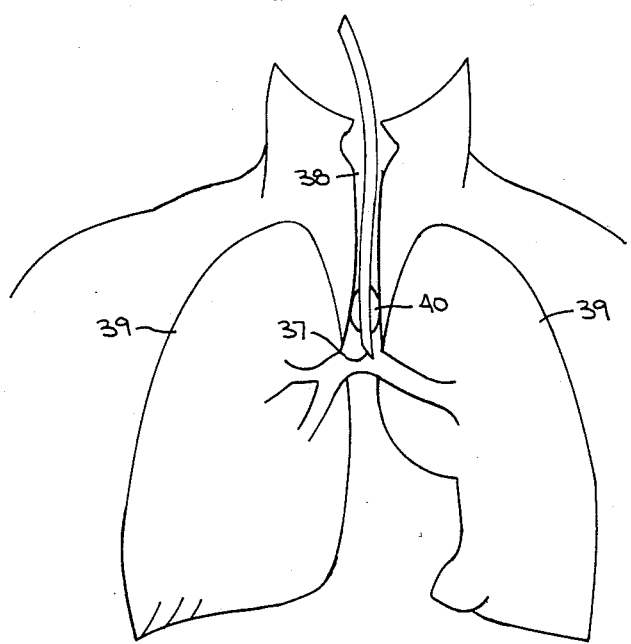
FIG. 17 is a diagramatic illustration showing use of the endotracheal tube of FIG. 16 as placed in the trachea of a mammal.

Another embodiment provides a laser shield wherein water bubbles and glass bubbles are both encapsulated in silicone. The photo micrographs of FIGS. 8–10 illustrate water and glass bubbles which are encapsulated in silicone. In some cases, the glass bubbles are enclosed in a water bubble which, in turn, is encapsulated by silicone. The micro-photograph of FIG. 10 illustrates how the laser shield which employs encapsulated water and glass bubbles has terminated two separate incidences of laser energy.

The use of bubbles and/or encapsulated water has been found to eliminate the issuance of black films possibly containing carbon or carcinogenics which are sometimes produced by silicone alone when subjected to laser energy. Thus, the laser shield which encapsulates densely packed bubbles and/or layers of water within silicone is an extremely desirable laser shield for use in medical applications. For example, a surgical drape 25 includes a flexible and lightweight sheet-like material 26 which is to be applied adjacent to an area subject to laser radiation and is formed of a series of densely packed bubbles encapsulated in a matrix of silicone. A fabric sheet 27, such as conventionally used in surgery, is attached by adhesive or other suitable fastening means to the laser terminating material 26 to form the surgical drape 25. Such surgical drape 25 may be safely used in areas where laser energy is being applied to a patient so as to shield the patient from unintended laser radiation, such as might occur by the accidiential movement of the laser source.

A surgical sponge 30 includes a flexible and lightweight sheet-like material 31 formed of a series of densely packed bubbles encapsulated in a matrix of silicone to terminate laser radiation. A pair of sheet-like sponges 32 and 33 are attached to opposite sides of the laser terminating material 31 to form a small pad which can be cut into any desired configuration and placed within or near an organ which is being treated or operated upon by laser energy.

An endotracheal tube 35 has first and second oppositely spaced openings 36 and 37 to permit the passage of anethetic gases therethrough and is formed of a flexible and lightweight material having a series of densely packed bubbles encapsulated in a matrix of silicone to terminate laser radiation that may strike the elongated tube. The endotracheal tube 35 may be inserted into an esophagus 38 so that end 37 is located adjacent to the lungs 39 while a balloon 40 receives pressurizing gas through a balloon inflation tube 41 to provide an airtight seal between the endotracheal tube 35 and the esophagus 38. Thereafter, a laser transmitting apparatus is inserted into the body cavity adjacent to the endotracheal tube 35 and laser energy is transmitted with the result that any unintended laser energy which impinges the side walls of the endotracheal tube 35 will be terminated, preventing combustion of the anesthetic gases within the endotracheal tube.

It is contemplated that when glass bubbles are utilized, a flame retardant gas, such as an inert gas, may be placed therein to further suppress laser energy.

Various modes of carrying out the invention are contemplated as being within the scope of the following claims which particularly point out and distinctly claim the subject matter which is regarded as the invention.

We claim:

1. A laser shield, consisting essentially of a dispersion of water in liquid droplet form encapsulated in a matrix of silicone rubber to provide a flexible material to terminate laser radiation without producing a substantial carbon plume.

2. A laser shield, comprising a matrix of silicone rubber, and a dispersion of densely packed bubbles encapsulated in said silicone rubber for providing protection from laser radiation, said bubbles are densely packed within a range of $1.95 \times 10^3$ bubbles per cubic centimeter to $1.25 \times 10^8$ bubbles per cubic centimeter, with at least a portion of said bubbles including water in liquid droplet form.

3. A surgical drape, comprising a flexible and light weight sheet material to be applied adjacent to an area subject to laser radiation and formed of a dispersion of densely packed bubbles encapsulated in a matrix of silicone rubber to terminate laser radiation, said bubbles include glass bubbles and water in liquid droplet form.

4. A surgical drape, comprising a flexible and light weight sheet material to be applied adjacent to an area subject to laser radiation and formed of a dispersion of densely packed bubbles encapsulated in a matrix of silicone rubber to terminate laser radiation, said bubbles include water in liquid droplet form.

* * * * *